United States Patent
Asgharian

(10) Patent No.: US 6,486,215 B2
(45) Date of Patent: Nov. 26, 2002

(54) SOLUTIONS FOR TREATING CONTACT LENSES

(75) Inventor: Bahram Asgharian, Arlington, TX (US)

(73) Assignee: Alcon Manufacturing, Ltd., Fort Worth, TX (US)

(*) Notice: Subject to any disclaimer, the term of this patent is extended or adjusted under 35 U.S.C. 154(b) by 0 days.

(21) Appl. No.: 09/883,676

(22) Filed: Jun. 18, 2001

(65) Prior Publication Data

US 2001/0046973 A1 Nov. 29, 2001

Related U.S. Application Data

(62) Division of application No. 09/765,234, filed on Jan. 18, 2001, which is a continuation of application No. 09/242,640, filed as application No. PCT/US98/14597 on Jul. 17, 1998, now abandoned.

(60) Provisional application No. 60/054,119, filed on Jul. 29, 1997.

(51) Int. Cl.$^7$ .................... A61K 31/715; C07H 1/00
(52) U.S. Cl. .................... 514/839; 514/912; 514/22; 514/944; 514/54; 536/123.1; 536/124; 536/128
(58) Field of Search ............................ 514/22, 944, 54, 514/839, 912; 536/123.1, 124, 128

(56) References Cited

U.S. PATENT DOCUMENTS

| 3,884,826 A | 5/1975 | Phares, Jr. et al. |
| 3,960,150 A | 6/1976 | Hussain et al. |
| 4,136,173 A | 1/1979 | Pamoda et al. |
| 4,136,177 A | 1/1979 | Lin et al. |
| 4,136,178 A | * 1/1979 | Lin et al. |
| 4,242,239 A | 12/1980 | Kessler et al. |
| 4,255,415 A | 3/1981 | Chrai et al. |
| 4,259,202 A | 3/1981 | Tanaka et al. |
| 4,323,467 A | 4/1982 | Fu |
| 4,407,791 A | 10/1983 | Stark |
| 4,436,730 A | 3/1984 | Ellis et al. |
| 4,500,441 A | 2/1985 | Tanaka et al. |
| 4,525,346 A | 6/1985 | Stark |
| 4,619,776 A | 10/1986 | Mondshine |
| 4,645,833 A | 2/1987 | Bayerlein et al. |
| 4,734,222 A | 3/1988 | Winterton et al. |
| 4,745,184 A | 5/1988 | Bayerlein et al. |
| 4,748,189 A | 5/1988 | Su et al. |
| 4,758,595 A | 7/1988 | Ogunbiyi et al. |

(List continued on next page.)

FOREIGN PATENT DOCUMENTS

| EP | 0 227 494 A1 | 7/1987 |
| EP | 0 279 378 A1 | 8/1988 |
| EP | 0 386 960 A2 | 9/1990 |
| EP | 0 427 548 A2 | 5/1991 |
| JP | 10221654 | 8/1998 |
| WO | WO 94/10976 | 5/1994 |
| WO | WO 97/30092 | 8/1997 |
| WO | WO 99/06023 | 2/1999 |
| WO | WO 99/06070 | 2/1999 |

OTHER PUBLICATIONS

Kesavan et al., "Rheology of guar and (hydroxypropyl) guar crosslinked by borate", Macromolecules, vol. 25(7): 2026–2032.*

(List continued on next page.)

Primary Examiner—Ralph Gitomer
Assistant Examiner—Devesh Khare
(74) Attorney, Agent, or Firm—Gregg C. Brown

(57) ABSTRACT

Contact lens care compositions for the treatment of hard contact lenses are disclosed. The compositions are useful for rinsing, cleaning, disinfecting and storing of hard contact lenses. The compositions contain an unique gelling system involving galactomannan polysaccharides and borates to allow for the conditioning of the lens when it is reinserted in the eye of the user. Methods of using these compositions are also disclosed.

34 Claims, 3 Drawing Sheets

EFFECT OF GUAR GUM CONCENTRATION ON VISCOSITY
BORIC ACID FIXED AT 0.5% (w/v)

U.S. PATENT DOCUMENTS

| | | |
|---|---|---|
| 4,820,352 A | 4/1989 | Reidhammer et al. |
| 4,836,986 A | 6/1989 | Ogunbiyi et al. |
| 4,861,760 A | 8/1989 | Mazuel et al. |
| 5,082,579 A | 1/1992 | Dawson |
| 5,145,590 A | 9/1992 | Dawson |
| 5,160,643 A | 11/1992 | Dawson |
| 5,260,021 A | 11/1993 | Zeleznick |
| 5,273,580 A | 12/1993 | Totten et al. |
| 5,310,429 A | 5/1994 | Chou et al. |
| 5,318,780 A | 6/1994 | Viegas et al. |
| 5,342,620 A * | 8/1994 | Chowhan et al. |
| 5,372,732 A | 12/1994 | Harris et al. |
| 5,439,057 A | 8/1995 | Weaver et al. |
| 5,476,540 A | 12/1995 | Shields et al. |
| 5,505,953 A | 4/1996 | Chowhan |
| 5,593,637 A | 1/1997 | Mowrey-McKee et al. |
| 5,607,698 A | 3/1997 | Martin et al. |
| 5,658,861 A | 8/1997 | Nelson et al. |
| 5,672,213 A | 9/1997 | Asgharian et al. |
| 5,773,025 A | 6/1998 | Baichwal |
| 5,804,213 A | 9/1998 | Rolf |
| 5,811,466 A | 9/1998 | Chowhan et al. |
| 5,817,277 A | 10/1998 | Mowrey-McKee et al. |
| 5,919,313 A | 7/1999 | Asgharian et al. |
| 5,919,742 A | 7/1999 | Tsuzuki et al. |
| 6,005,031 A | 12/1999 | Bremer-Masseus et al. |

OTHER PUBLICATIONS

Noble et al., "Complex formation between guar D–galacto–D–mannan and borate ion. Thermodynamic data." Carbohydrate Research, vol. 184:236–243.*

Carbohydrate Chemistry, edited by John F. Kennedy, publ. by Clarendon Press, pp. 231–240, 624 and 625.

Carbohydrates in Food, edited by Ann–Charlotte Eliasson, publ. by Marcel Dekker, pp. 294–297.

Dumitriu et al., "Hydrogels based on polysaccharides", Polysaccharides in Medicinal Applications, edited by Severian Dumitriu, publ. by Marcel Dekker, pp. 171–183.

Gey et al., "Borate complexes of guar galactomannan polymer and related model compounds", Food Hydrocoloids, vol. 1(506): 593–595.

Pezron et al., "Galactomannan–borate systems: a complexation study", Biol. Synth. Poly. Networks, editor Kramer, Ole, publ. Elsevier, pp. 113–126.

"Pharmaceutical Dosage Forms and Drug Delivery System", pp. 110–116 (1995).

Power et al., "Gel transition studies on nonideal polymer networks using small amplitude oscillatory rheometry", J. Rheol., vol. 42(5): 1021–1037.

* cited by examiner

SOLUTIONS FOR TREATING CONTACT LENSES

The present application is a divisional of Ser. No. 09/765,234 filed Jan. 18, 2001, which is a continuation of a 371 application, Ser. No. 09/242,640 filed Feb. 16, 1999 (now abandoned), which is a 371 to PCT/US98/14597 filed Jul. 17, 1998, and Provisional Application No. 60/054,119 filed Jul. 29, 1997.

BACKGROUND OF THE INVENTION

The present invention relates to contact lens care compositions useful in treating hard contact lenses. The compositions of the present invention involve an unique polymer gelling system comprising a galactomannan polysaccharide and a borate crosslinking compound, which together form a mucin-like soft gel in the presence of increasing pH and ionic strength.

Hard contact lenses are named for their rigidity, and are generally made of polymethyl methacrylate (PMMA), siloxane acrylates, fluoro-siloxane acrylates or fluoro polymers. The most common type of hard contact lenses are the rigid gas permeable ("RGP") lenses, which allow soluble gases contained in natural or artificial tears to pass through it and feed the corneal tissues.

Hard contact lenses require periodic cleaning and disinfecting before they can be reused by the wearer. Numerous cleaning, rinsing, disinfecting and storing solutions have been used in the past. In general, these solutions have contained one or more antimicrobial agents, salts, buffers, surfactants and conditioning agents. Conditioning agents are useful in hard contact lens care solutions because they assist in lubricating the lenses. When hard contact lenses are inserted in the eye they can cause discomfort to the user due to the relatively hydrophobic surface and rigid nature of the lenses. Thus, cleaning and conditioning solutions which provide lubricating conditioners are particularly useful in hard contact lens care. Conditioning compositions often are multi-functional solutions designed to be used for wetting, soaking and disinfection of hard contact lenses.

Hard contact lenses have limited water retention capability and do not wet adequately when placed in solutions or inserted in the eye. Current technology teaches that the application of natural or synthetic water soluble polymers to the surfaces of hard contact lenses not only increases the wettability of the lenses, but also provides a "cushion" layer between the lens and the eye. These polymer adsorptions have been equated with increased wettability as well as user comfort and tolerance. Dissipation of the "cushion" layer, however, occurs rapidly in most prior art constructions, since there is little specific interaction between the mobile polymer in this layer and the lens surface. As a result, the wearer begins to feel discomfort and must rewet the lens surface.

Surface-active agents have been employed in conditioning solutions in an attempt to alleviate the above-described problems. Surface-active agents are adsorbed on the lens surface and allow ready spreading of tears when the lenses are inserted, thus making them more comfortable to wear. Representative wetting agents and viscosity modifiers have included: cellulose derivatives, such as cationic cellulosic polymers, hydroxypropyl methylcellulose, hydroxyethylcellulose and methylcellulose; polyols, such as polyethylene glycol, glycerine and polyethylene oxide (PEO) containing polymers; polyvinyl alcohol; and polyvinyl pyrrolidone. Such additives may be used in a wide range of concentrations as is known in the art. These types of agents, however, do not adsorb to a significant level to the lens, and therefore do not provide prolonged comfort.

Polymers which provide a more prolonged comfort level typically need to be employed in high concentration to create a higher viscosity, and thereby prolong the retention of the polymer. The use of these high viscosity agents, however, may cause blurring of vision when the lens is first placed in the eye, and also creating a sticky feeling of the lens to the user, making lens insertion and handling difficult. More hydrophobic polymers can adsorb more readily to the lens, and can be formulated at lower concentrations to provide better lubrication. The disadvantage, however, of a more hydrophobic polymer is that the polymer may also act as a substrate for deposits and as a consequence, make the lens more prone to filming and lipid deposit.

Various cleaning, disinfecting and storing solutions have been described in the art. For example, the use of antimicrobial agents like quaternary amonionium polymers, and particularly, polyquaternium-1, have been described in U.S. Pat. No. 4,407,791 (Stark) and U.S. Pat. No. 4,525,346 (Stark). U.S. Pat. No. 4,758,595 (Ogunbiyi) and U.S. Pat. No. 4,836,986 (Ogunbiyi) have described the use of polymeric biguanides in disinfecting solutions. Various contact lens care solutions containing lubricants for conditioning hard contact lenses have also been disclosed in the patent literature. For example, U.S. Pat. No. 4,436,730 (Ellis et al.) discloses compositions for wetting, soaking and lubricating lenses, and U.S. Pat. No. 4,820,352 (Riedhammer et al.) and U.S. Pat. No. 5,310,429 (Chou et al.) disclose compositions for cleaning and lubricating lenses.

Various gelling compositions have been described in the art for use in ophthalmic applications. In general, these types of systems have been used for the topical application of pharmaceuticals, wherein the topical solution partially or fully gels upon instillation in the eye, to allow for a sustained release of the pharmaceutical agent to the eye. Such agents have included the use of polyvinyl alcohols, euchema gels, xanthan gums and gellan gum. However, stimuli sensitive polymer systems for treating contact lenses have not been disclosed in the art.

The use of current gelling systems have a number of drawbacks for use in contact lens care applications. U.S. Pat. No. 4,136,173 (Pramoda, et al.) and U.S. Pat. No. 4,136,177 (Lin, et al.) disclose the use of therapeutic compositions containing xanthan gum and locust bean gum which are administered in liquid form and gel upon instillation. These disclosures describe a mechanism for transition from liquid to gel involving pH change. pH sensitive gels such as carbomers, xanthan, gellan, and those described above, need to be formulated at or below the pKa of their acidic groups (typically at a pH of about 2 to 5). Compositions formulated at low pH, however, are irritating to the eye. U.S. Pat. No. 4,861,760 (Mazuel, et al.) discloses ophthalmic compositions containing gellan gum which are administered to the eye as non-gelled liquids and gel upon instillation due to a change in ionic strength. These systems do not involve the use of small cross-linking molecules, but instead provide gel characteristics due to self cross-linking during ionic condition changes.

Current polymer gel systems, however, have a number of disadvantages. Contact lens conditioning solutions are typically formulated as multi-functional compositions which disinfect and condition the lens simultaneously. These multi-purpose solutions will typically employ an polymeric cationic antimicrobial agent. Anionic polymers electrostatically interact with polymeric cationic antimicrobials, such as polyquaternium-1 and PHMB. This interaction interferes with the disinfecting activity of the antimicrobial agents, and the disinfecting efficacy of the solutions may therefore be compromised. Ion sensitive gels such as gellan, carageenan and xanthan are capable of forming gels when they are used at a relatively high viscosity (high concentration) of about 100 to 1000 centiposes ("cps"). This viscosity range, however, is generally too high for ease of lens handling and visual clarity.

Gels involving the cross-linking of polysaccharides with borates are disclosed for use as well fracturing fluids in U.S. Pat. Nos. 5,082,579, and 5,160,643. These patents describe the use of borates and polysaccharides for industrial oil well excavation.

The use of other gelling systems for contact lens care applications also have a number of drawbacks. For example, natural polymers such as xanthan gum have the disadvantage of lot to lot variability due to variations in source and/or limited manufacturing controls during processing. These variabilities cause significant undesirable changes in the properties of the compound, such as variable gelling characteristics. Thermogelling systems such as polyethylene oxide/ polypropylene oxide block copolymers ("PEO/PPO") lose water in order to form gels, and consequently result in turbid gels.

Polyvinyl alcohol-borate crosslinking gels have been disclosed in U.S. Pat. No. 4,255,415 (Sukhbir et al.) for ophthalmic drug delivery. These compositions are pre-formed gels, and are therefore difficult to dispense. WIPO Publication No. WO 94/10976 (Goldenberg et al.) discloses a low pH PVA-borate delivery system that does go through liquid/gel transition. This system has the disadvantage, however, of limited gelling effects, and only at certain concentrations of PVA depending on the molecular weight of the PVA utilized. Furthermore, since the crosslinking cites are unlimited with this system, strong local gelation upon addition of base has limited its manufacturing and, therefore, polyvinyl pyrrolidone presumably has been included in these compositions to overcome the shortcoming. The novel gelling system of the present invention does not have the above limitation.

What is needed, therefore, are rinsing, disinfecting, cleaning, storing and conditioning solutions for hard contact lenses which provide the necessary cleaning, disinfecting, rinsing, storing and conditioning efficacies and which provide ease of handling and comfort to the user when the lenses are inserted in the eye and worn.

SUMMARY OF THE INVENTION

The present invention is directed to contact lens care solutions useful in treating hard contact lenses. More specifically, the present invention is directed to compositions useful in rinsing, disinfecting, cleaning, storing and conditioning hard contact lenses. The compositions of the present invention comprise an unique gelling system involving galactomannan polysaccharides and a borate source.

The compositions of the present invention are low viscosity, clear solutions and provide excellent characteristics for manual manipulation of the lens. Once the lens is soaked in a composition of the present invention, the galactomannan polysaccharide adsorbs on the lens, and upon insertion in the eye, a soft, clear gel is formed which mimics the natural mucin present in the eye. The gel provides reduced drainage of the polymer through the ocular cavities due to the intermolecular crosslinking of the polymer, via borate crosslinking. Additionally, the polysaccharide-borate gels disclosed herein have far better lubricating efficacy over non-crosslinking polymer systems.

The gelling system of the present invention provides excellent reproducibility in the manufacturing process, and also excellent gelling characteristics including the ocular clarity of the resultant gel. Moreover, as illustrated in FIG. 3, the galactomannans of the present invention (e.g., guar gum) demonstrate excellent gelling consistency and reproducibility, though the type or source of the galactomannan is varied.

The present invention is also directed to methods for using the compositions of the present invention to rinse, disinfect, clean and condition hard contact lenses.

The present invention is also directed to methods of sterilization of the galactomannans involving autoclaving.

DETAILED DESCRIPTION OF THE INVENTION

The present invention is directed to contact lens care compositions which comprise one or more galactomannan polysaccharide(s) and one or more borate compound(s). The present invention is also directed to methods of using these compositions to rinse, disinfect, clean and condition contact lenses.

The types of galactomannans that may be used in the present invention are typically derived from guar gum, locust bean gum and tara gum. As used herein, the term "galactomannan" refers to polysaccharides derived from the above natural gums or similar natural or synthetic gums containing mannose or galactose moieties, or both groups, as the main structural components. Preferred galactomannans of the present invention are made up of linear chains of $(1-4)$-$\beta$-D-mannopyranosyl units with $\alpha$-D-galactopyranosyl units attached by (1–6) linkages. With the preferred galactomannans, the ratio of D-galactose to D-mannose varies, but generally will be from about 1:2 to 1:4. Galactomannans having a D-galactose:D-mannose ratio of about 1:2 are most preferred. Additionally, other chemically modified variations of the polysaccharides are also included in the "galactomannan" definition. For example, hydroxyethyl, hydroxypropyl and carboxymethylhydroxypropyl substitutions may be made to the galactomannans of the present invention. Non-ionic variations to the galactomannans, such as those containing alkoxy and alkyl (C1–C6) groups are particularly preferred (e.g., hydroxylpropyl substitutions). Substitutions in the non-cis hydroxyl positions are most preferred. An example of non-ionic substitution of a galactomannan of the present invention is hydroxypropyl guar, which is preferably substituted up to about a 0.6 molar ratio.

The borate compounds which may be used in the compositions of the present invention are boric acid and other pharmaceutically acceptable salts such as sodium borate (borax) and potassium borate. As used herein, the term "borate" refers to all pharmaceutically suitable forms of borates. Borates are common excipients in ophthalmic formulations due to good buffering capacity at physiological pH and well known safety and compatibility with wide range of drugs and preservatives. Borates also have inherent bacteriostatic and flugistatic properties which provide improved preservative systems. Since borates possess minimal buffering effect below pH 7.0, the pH of the contact lens care solution can easily be adjusted by retinal tears, upon instillation to the eye.

Figure 1:
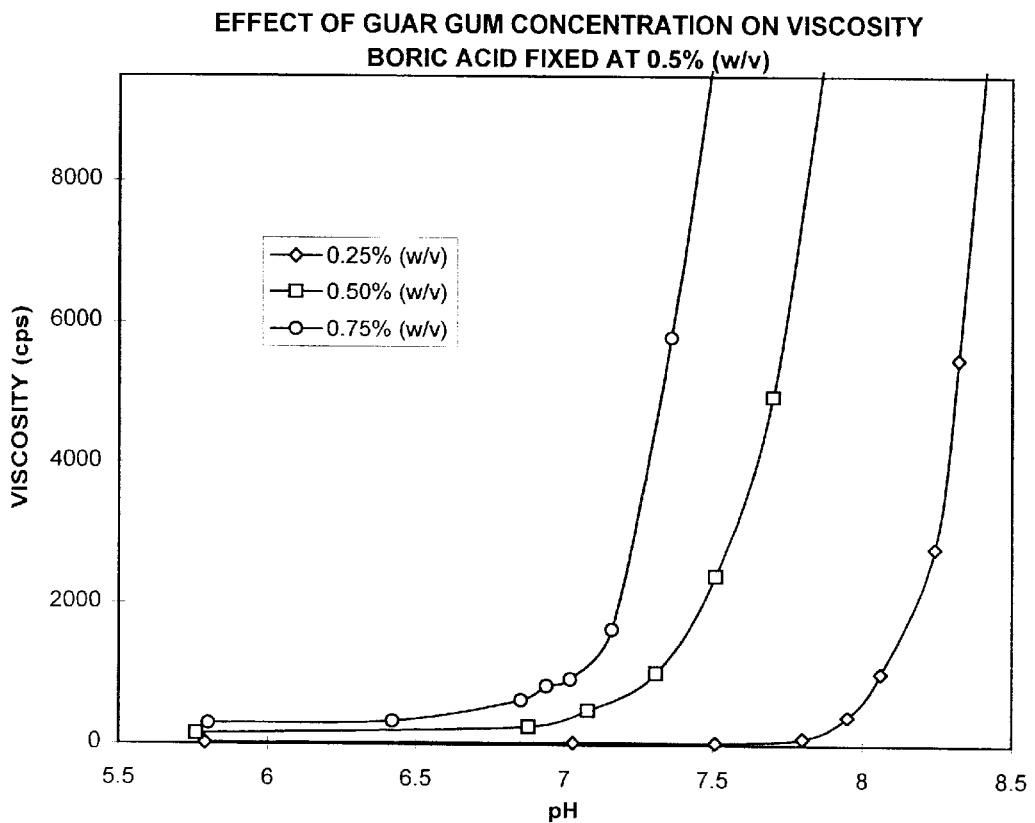
FIG. 1 is a graph illustrating the gelling characteristics of various concentrations of guar gum in the presence of borate, relative to pH.
Figure 2:
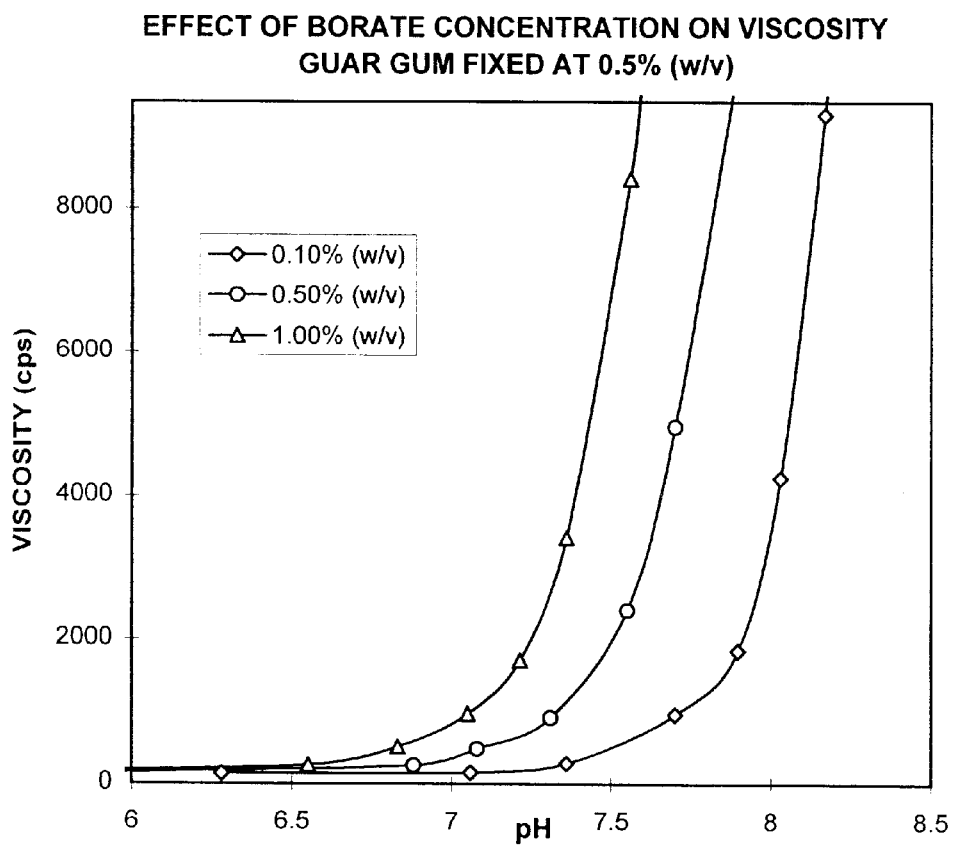
FIG. 2 is a graph illustrating the gelling characteristics of various concentrations of borate in the presence of guar gum, relative to pH.
Figure 3:
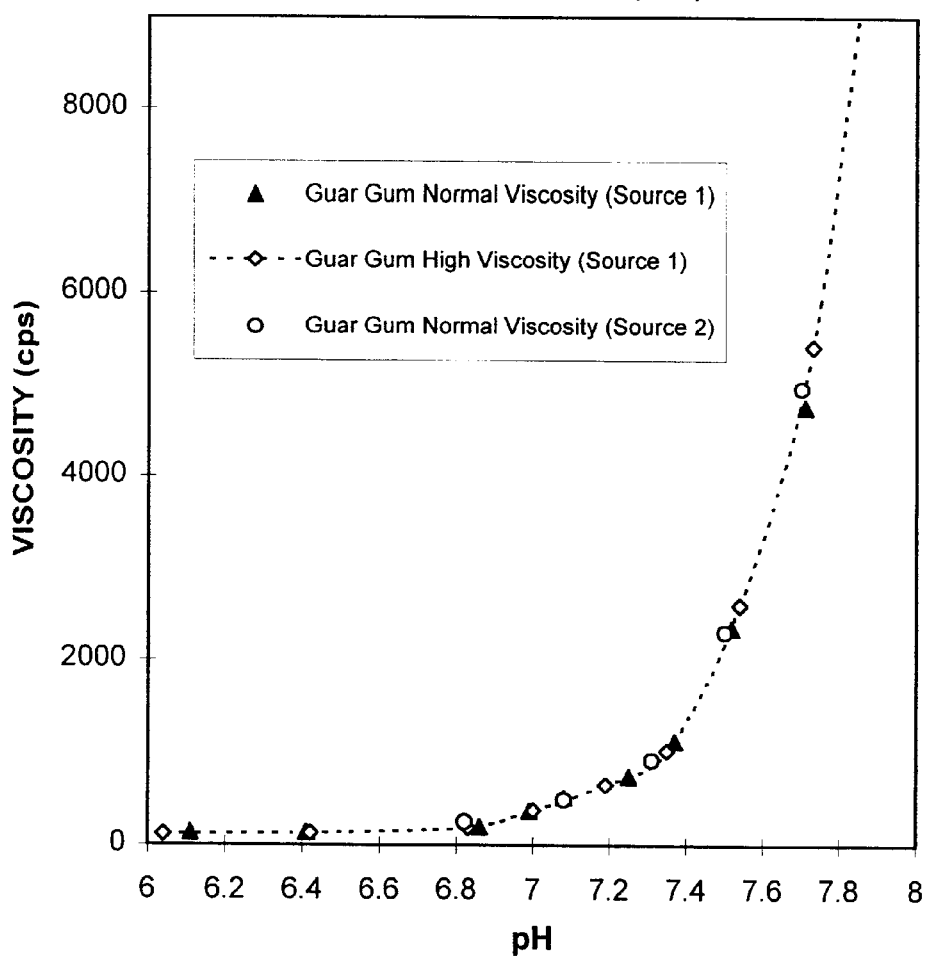
FIG. 3 is a graph illustrating uniformity of the gelling characteristics of three different types/sources of guar gum.

The present invention compositions comprise one or more galactomannan(s) in the amount of from 0.1 to 2.0% weight/volume ("w/v") and borate in the amount of from 0.05 to 2% (w/v). Preferably, the compositions will contain 0.1 to 1.0% (w/v) of galactomannan and 0.1 to 1.0% (w/v) of a borate compound. Most preferably, the compositions will contain 0.2 to 0.5% (w/v) of galactomannan and 0.2 to 0.75% (w/v) of a borate compound. The particular amounts will vary, depending on the particular gelling properties desired. In general, the borate or galactomannan concentration may be manipulated in order to arrive at the appropriate viscosity of the composition upon gel activation (i.e., after administration). As shown in FIGS. 1 and 2, manipulating either the borate or galactomannan concentration provides stronger or weaker gelation at a given pH. If a strongly gelling composition is desired, then the borate or galactomannan concentration may be increased. If a weaker gelling composition is desired, such as a partially gelling composition, then the borate or galactomannan concentration may be reduced. Other factors may influence the gelling features of the compositions of the present invention, such as the nature and concentration of additional ingredients in the compositions, such as salts, preservatives, chelating agents and so on. Generally, preferred non-gelled conditioning solutions of the present invention, i.e., conditioning solutions not yet gel-activated by the eye, will have a viscosity of from about 5 to 100 cps. Generally, a gelled composition of the present invention will have a viscosity of about 10 to 1000 cps.

The galactomannans of the present invention may be obtained from numerous sources. Such sources include guar gum, locust bean gum and tara gum, as further described below. Additionally, the galactomannans may also be obtained by classical synthetic routes or may be obtained by chemical modification of naturally occurring galactomannans.

Guar gum is the ground endosperm of *Cyamopisis tetragonolobus* (L.) Taub. The water soluble fraction (85%) is called "guaran" (molecular weight of 220,000), which consists of linear chains of (1–4)-β-D mannopyranosyl units with α-D-galactopyranosyl units attached by (1–6) linkages. The ratio of D-galactose to D-mannose in guaran is about 1:2. The gum has been cultivated in Asia for centuries and is primarily used in food and personal care products for its thickening property. It has five to eight times the thickening power of starch. Its derivatives, such as those containing hydroxypropyl or hydroxypropyltrimonium chloride substitutions, have been commercially available for over a decade. Guar gum can be obtained, for example, from Rhone-Polulenc (Cranbury, N.J.), Hercules, Inc. (Wilmington, Del.) and TIC Gum, Inc. (Belcamp, Md.).

Locust bean gum or carob bean gum is the refined endosperm of the seed of the carob tree, ceratonia siliqua. The ratio of galactose to mannose for this type of gum is about 1:4. Cultivation of the carob tree is old and well known in the art. This type of gum is commercially available and may be obtained from TIC Gum, Inc. (Bekamp, Md.) and Rhone-Polulenc (Cranbury, N.J.).

Tara gum is derived from the refined seed gum of the tara tree. The ratio of galactose to mannose is about 1:3. Tara gum is not produced in the United States commercially, but the gum may be obtained from various sources outside the United States.

In order to limit the extent of cross-linking to provide a softer gel characteristic, chemically modified galactomannans such as hydroxypropyl guar may be utilized. Modified galactomannans of various degree of substitution are commercially available from Rhone-Poulenc (Cranbury, N.J.). Hydroxypropyl guar with low molar substitution (e.g., less than 0.6) is particularly preferred.

The compositions of the present invention will contain other ingredients. Such ingredients include antimicrobial/preservative agents, tonicity adjusting agents, buffers and chelating agents. Other polymer or monomeric agents such as polyethylene glycol, and glycerol may also be added for special processing. Tonicity adjusting agents useful in the compositions of the present invention may include salts such as sodium chloride, potassium chloride and calcium chloride; non-ionic tonicity agents may include propylene glycol and glycerol; chelating agents may include EDTA and its salts; and pH adjusting agents may include hydrochloric acid, Tris, triethanolamine and sodium hydroxide. Suitable anti-microbial agents/preservatives are discussed more fully below. The above listing of examples is given for illustrative purposes and is not intended to be exhaustive. Examples of other agents useful for the foregoing purposes are well known in contact lens care formulation and are contemplated by the present invention.

Combination of the gelling system of the present invention with prior art gelling systems is also contemplated by the present invention. Such systems may include the inclusion of ionamers, such as, xanthan, gellan, carageenan, carbamers; and thermogels, such as, ethylhydroxyethyl cellulose.

The disinfecting compositions of the present invention will contain an antimicrobial agent. Antimicrobial agents may be either monomeric or polymeric antimicrobial agents which derive their antimicrobial activity through a chemical or physicochemical interaction with the organisms. As used in the present specification, the term "polymeric antimicrobial agent" refers to any nitrogen-containing polymer or co-polymer which has antimicrobial activity. Preferred polymeric antimicrobial agents include: polyquaternium-1, which is a polymeric quaternary ammonium compound; and polyhexamethylene biguanide ("PHMB") or polyaminopropyl biguanide ("PAPB"), which are polymeric biguanides. These preferred antimicrobial agents are disclosed in U.S. Pat. Nos. 4,407,791 and 4,525,346, issued to Stark, and U.S. Pat. Nos. 4,758,595 and 4,836,986, issued to Ogunbiyi, respectively. The entire contents of the foregoing publications are hereby incorporated in the present specification by reference. Other antimicrobial agents suitable in the compositions and methods of the present invention include: other quaternary ammonium compounds, such as benzalkonium halides, and other biguanides, such as chlorhexidine. The antimicrobial agents used herein are preferably employed in the absence of mercury-containing compounds such as thimerosal. Particularly preferred antimicrobial agents of the present invention are polymeric quaternary ammonium compounds of the structure:

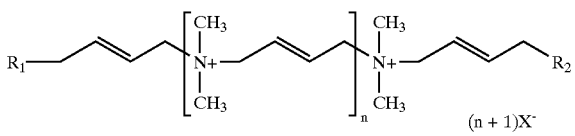

wherein:
  $R_1$ and $R_2$ can be the same or different and are selected from:
    $N^+(CH_2CH_2OH)_3X^-$,
    $N(CH_3)_2$ or OH;
  X is a pharmaceutically acceptable anion, preferably chloride; and
  n=integer from 1 to 50.

The most preferred compounds of this structure is polyquaternium-1, which is also known as Onamer M™ (registered trademark of Onyx Chemical Corporation) or as Polyquad® (registered trademark of Alcon Laboratories, Inc.). Polyquaternium-1 is a mixture of the above referenced compounds, wherein X is chloride and $R_1$, $R_2$ and n are as defined above.

The above-described antimicrobial agents are utilized in the methods of the present invention in an amount effective to eliminate substantially or to reduce significantly the number of viable microorganisms found on contact lenses, in accordance with the requirements of governmental regulatory agencies, such as the United States Food and Drug Administration. For purposes of the present specification, that amount is referred to as being "an amount effective to disinfect" or "an antimicrobially effective amount." The amount of antimicrobial agent employed will vary, depending on factors such as the type of lens care regimen in which the method is being utilized. For example, the use of an efficacious daily cleaner in the lens care regimen may substantially reduce the amount of material deposited on the lenses, including microorganisms, and thereby lessen the amount of antimicrobial agent required to disinfect the lenses. In general, a concentration in the range of about 0.000001% to about 0.05% by weight of one or more of the above-described antimicrobial agents will be employed. The most preferred concentration of the polymeric quaternary ammonium compounds of Formula (I) is about 0.0001% to 0.001 by weight.

In general, the compositions of the present invention are formulated in two parts. The galactomannan polymer is hydrated and sterilized (Part I). The other ingredients to be included in the composition are then dissolved in water and sterile filtered (Part II). Parts I and II are then combined and the pH of the resultant mixture is adjusted to the target level, generally 6.5 to 7.2.

The compositions of the present invention may also be formulated as multi-purpose compositions, i.e., compositions that also provide daily cleaning efficacy. Such multi-purpose compositions will typically contain surfactant(s), in addition to conditioning and disinfection. Surfactants useful in these compositions include poloxamines, poloxamers, alkyl ethoxylates, alkyl phenyl ethoxylates or other nonionic, anionic and zwitterionic surfactants known in the art.

Sterilization of the galactomannan polysaccharide can be accomplished by autoclaving. Since the polymer undergoes depolymerization at the extreme conditions of autoclaving, non aqueous autoclaving is generally preferred. This can be accomplished by dispersing the polymer in a suitable organic liquid such as low molecular weight polyethylene glycols. The resulting suspension may then be autoclaved to sterilize the polymer. The sterilized polymer is then hydrated aseptically, prior to admixture with the other ingredients. Alternatively, the polymer powder may be sterilized by dry heat. The following example illustrates a novel method of sterilizing a galactomannan polysaccharide of the present invention:

EXAMPLE 1

This example illustrates a method of preparing the following multi-purpose, conditioning solution of the present invention:

| Ingredient | Concentration (% W/V) | Amount per 20 liters |
|---|---|---|
| Hydroxypropyl Guar Gum | 0.20 | 40 g |
| Polyethylene Glycol 400 | 0.40 | 80 g |
| Tetronic 1304 | 0.25 | 50 g |
| Boric Acid | 1.00 | 200 g |
| Propylene Glycol | 0.90 | 180 g |
| Disodium Edetate | 0.01 | 2 g |
| Polyquaternium-1 | 0.001 + 50% Excess | 0.3 g (100%) |
| Sodium Hydroxide and/or Hydrochloric Acid | adjust pH (6.8–7.2) (target 7.0) | n/a |
| Purified Water | QS 100% | QS 20 liters or 20.06 kg |

Preliminarily, a compounding vessel (20 L stainless steel pressure can), a 0.2 micron sterilizing filter, a receiving vessel (20 L carboy), a 4.5 micron polishing filter, a 0.2 micron sterilizing filter, a vent filter, and the filling equipment are sterilized by autoclaving.

In a beaker equipped with an overhead agitator, add the weighed amount of polyethylene glycol 400 (200 g). While mixing slowly disperse the weighed amount of hydroxypropyl ("HP") Guar gum (100 g). Mix until completely homogeneous. In a 500 ml Schott bottle, equipped with a magnetic stir bar, weigh exactly 120.0 g of the HPGuar gum/PEG-400 dispersion. Prepare to sterilize by autoclaving. In a second identical 500 ml Schott bottle weigh exactly 120.0 g of the same dispersion. Prepare to use as a dummy during the autoclaving cycle. To both bottles add 1.3 ml of purified water (amount equivalent, by volume, of the microorganism suspension used to inoculate the bottles during the validation study). Mix both bottles for 10 minutes using a magnetic stir plate. Autoclave the HPGuar gum/PEG-400 dispersion using the validated time-temperature cycle of 80 minutes at 125° C.

In a vessel equipped with an overhead agitator, add purified water equivalent to approximately 70% of the theoretical batch weight (approximately 14 Kg). While mixing at moderate speed, slowly add the other ingredients desired: Tetronic 1304, Boric Acid, Propylene Glycol, Disodium Edetate. Mix for a minimum of 60 minutes, or until completely homogeneous. Check the temperature and, if necessary, cool to 35° C. or below. While mixing at low speed slowly add the Polyquaternium-1. Mix for a minimum of 15 minutes, or until completely homogeneous. Transfer into a pre-sterilized compounding vessel equipped with an agitator through a 0.2 micron sterilizing filter (the recommended compounding vessel is a pressure vessel and recommended agitator is an overhead mixer that can be used in sterile compounding area). Rinse the vessel and filter assembly with room temperature WFI.

Aseptically transfer the sterilized HPGuar gum/PEG-400 dispersion into the pre-sterilized compounding vessel. Rinse the bottle content with sterilized purified water. Bring the content of the compounding vessel to exactly 95% of the theoretical batch weight (19.0 liters or 19.06 Kg) using sterile room temperature purified water. Allow the HPGuar gum/PEG slurry to hydrate while mixing, at moderate speed, in the compounding vessel for a minimum of 2 hours. Transfer the contents of the compounding vessel through a 4.5 micron pre-sterilized polishing filter into the pre-sterilized receiving vessel equipped with a stir bar. There will be some loss of the contents due to the product held in filter housing and filter cartridge. (If a pressure can is used as compounding vessel, the recommended pressure for clarification filtration is approximately 30 psi.) Check and adjust pH, if necessary, to 6.9–7.1 (target 7.0) using 1N NaOH or 1N HCl. Approximately 3–4 ml of 1N NaOH per 1 liter of final batch weight is needed to achieve the desired pH. QS to final batch weight using sterile purified water. Mix at low speed for a minimum of 30 minutes.

The methods of the present invention will involve the use of one or more compositions of the present invention. If cleaning is desired, the soiled lens is generally placed in the palm of the user's hand, several drops of a multi-purpose composition of the present invention or optionally, another cleaning composition containing surfactants, is applied to the lens, and the lens is gently rubbed with the solution for a short period of time, generally 5 to 20 seconds. The cleaned lens may then be rinsed with a rinsing composition, such as a rinsing, disinfecting, cleaning and conditioning solution of the present invention, and placed in a lens case containing a volume of a rinsing, disinfecting and conditioning composition of the present invention. Generally, in order to disinfect and condition the lenses, they will be stored in a composition of the present invention for a period of about 4 hours to overnight.

The following examples further illustrate preferred compositions of the present invention:

EXAMPLE 2

A preferred conditioning, rinsing and disinfecting solution is described below:

| Ingredient | Concentration % (w/v) |
| --- | --- |
| Hydroxypropyl guar | 0.5 |
| Boric acid | 0.5 |
| Propylene glycol | 1.4 |
| Disodium Edetate | 0.015 |
| Polyquaternium-1 | 0.0003 |
| Sodium Hydroxide/Hydrochloric Acid | QS to pH 6.8 |
| Purified water | QS |

The above formulation may be made by first dispersing the polymer (hydroxypropyl guar) with high agitation into about 50% of the volume of water, allowing the polymer to hydrate (Part I). The polymer solution is then autoclaved at 121° C. for about 30 minutes. The remaining ingredients are then dispersed and dissolved into about 40% of the volume of water, and sterile filtered using a 0.2 micron filter, into a sterile container (Part II). The contents of Parts I and II are then combined aseptically and the pH is then adjusted. The batch is then brought to volume using additional purified water.

EXAMPLE 3

A preferred multi-purpose solution for daily cleaning, rinsing, disinfecting and conditioning is described below:

| Ingredient | Concentration % (w/v) |
| --- | --- |
| Hydroxypropyl guar | 0.2 |
| Tetronic 1304 | 0.25 |
| Boric acid | 1.0 |
| Propylene glycol | 0.9 |
| Disodium Edetate | 0.01 |
| Polyethylene glycol (400) | 0.4 |
| Polyquaternium-1 | 0.001 |
| Sodium Hydroxide/Hydrochloric Acid | QS to pH 6.8 |
| Purified water | QS |

The above formulation is prepared by first preparing a Part I and Part II mixture. The hydroxypropyl guar is dispersed in PEG-400 and autoclaved as Part I. The other ingredients are then dissolved in about 90% of the volume of water and sterile filtered into a receiving vessel as Part II. Part I is then added to Part I aseptically. The pH may then be adjusted aseptically, and the batch is then brought to final weight (volume). The combined solution is then passed through a 1.0 μm polish filter aseptically to remove any particulates. The resulting composition will have an osmoality of about 300 mOsm/kg and viscosity of about 16 cps.

EXAMPLE 4

A preferred multi-purpose solution for daily cleaning, rinsing, disinfecting and conditioning is described below:

| Ingredient | Concentration % (w/v) |
| --- | --- |
| Locust bean gum | 0.5 |
| Boric acid | 1.0 |
| Propylene glycol | 1.4 |
| Tetronic 1304 | 0.25 |
| Polyethylene glycol (400) | 1.0 |
| Polyquaternium-1 | 0.0005 |
| Sodium Hydroxide/Hydrochloric Acid | QS to pH 7.0 |
| Purified water | QS |

The above formulation may be prepared in a manner similar to the method described in example 3.

What is claimed is:

1. A solution for treating a contact lens, comprising:
    (a) a polymer gelling system comprising a galactomannan and a borate compound in amounts effective to create a gel or partial gel when the lens is coated with the solution and the lens is placed on an eye; and
    (b) water.

2. A solution according to claim 1, wherein the solution further comprises an effective amount of an ophthalmically acceptable antimicrobial agent.

3. A solution according to claim 2, wherein the antimicrobial agent is selected from the group consisting of polyquaternium-1 and polyhexamethylene biguanide.

4. A solution according to claim 1, wherein the galactomannan is selected from the group consisting of guar gum, locust bean gum, tara gum, and chemically modified derivatives thereof; and the borate compound is selected from the group consisting of boric acid, sodium borate, potassium borate and combinations thereof.

5. A solution according to claim 4, wherein the concentration of the galactomannan in the solution is 0.1 to 2.0% (w/v) and the concentration of the borate compound is 0.05 to 2.0% (w/v).

6. A solution according to claim 5, wherein the galactomannan comprises hydroxypropyl guar and the borate compound comprises boric acid.

7. A solution according to claim 6, wherein the solution contains hydroxypropyl guar in a concentration of 0.1 to 1.0% (w/v) and boric acid in a concentration of 0.1 to 1.0% (w/v).

8. A solution according to claim 7, wherein the solution further comprises an effective amount of an ophthalmically acceptable antimicrobial agent.

9. A solution according to claim 8, wherein the antimicrobial agent is selected from the group consisting of polyquaternium-1 and polyhexamethylene biguanide.

10. A solution according to claim 9, wherein the antimicrobial agent comprises polyquaternium-1.

11. A multi-purpose solution for treating a hard contact lens, comprising:
 (a) an ophthalmically acceptable antimicrobial agent in an amount effective to disinfect the lens;
 (b) a polymer gelling system comprising a galactomannan and a borate compound in amounts effective to create a gel or partial gel when the lens is coated with the solution and the lens is placed on an eye; and
 (c) water.

12. A multi-purpose solution according to claim 11, wherein the galactomannan is selected form the group consisting of guar gum, locust bean gum, tara gum and chemically modified derivatives thereof, and the borate compound is selected from the group consisting of boric acid, sodium borate, potassium borate and combinations thereof.

13. A multi-purpose solution according to claim 12, wherein the concentration of the galactomannan in the solution is about 0.1 to 2.0% (w/v) and the concentration of the borate compound is about 0.05 to 2.0% (w/v).

14. A multi-purpose solution according to claim 13, wherein the galactomannan comprises hydroxypropyl guar and the borate compound comprises boric acid.

15. A multi-purpose solution according to claim 14, wherein the solution contains hydroxypropyl guar in a concentration of 0.1 to 1.0% (w/v) and boric acid in a concentration of 0.1 to 1.0% (w/v).

16. A multi-purpose solution according to claim 15, wherein the antimicrobial agent comprises polyquaternium-1.

17. A solution for treating a contact lens, comprising:
 (a) an amount of a galactomannan effective to condition the lens; and
 (b) water.

18. A solution according to claim 17, wherein the galactomannan is selected from the group consisting of guar gum, locust bean gum, tara gum, and chemically modified derivatives thereof.

19. A solution according to claim 18, wherein the concentration of the galactomannan in the solution is 0.1 to 2.0% (w/v).

20. A solution according to claim 17, wherein the galactomannan comprises hydroxypropyl guar.

21. A solution according to claim 20, wherein the concentration of hydroxypropyl guar in the solution is 0.1 to 2.0% (w/v).

22. A solution according to claim 20, wherein the solution further comprises an ophthalmically acceptable antimicrobial agent in an amount effective to disinfect the lens.

23. A solution according to claim 22, wherein the antimicrobial agent is selected from the group consisting of polyquaternium-1 and polyhexamethylene biguanide.

24. A solution according to claim 23, wherein the antimicrobial agent comprises polyquaternium-1.

25. A solution according to claim 17, wherein the solution further comprises an ophthalmically acceptable antimicrobial agent in an amount effective to disinfect the lens.

26. A solution according to claim 25, wherein the antimicrobial agent is selected from the group consisting of polyquaternium-1 and polyhexamethylene biguanide.

27. A multi-purpose solution for cleaning, disinfecting and conditioning a contact lens, comprising:
 (a) a surfactant in an mount effective to clean the lens;
 (b) an amount of an ophthalmically acceptable antimicrobial agent effective to disinfect the lens;
 (c) a galactomannan in an amount effective to condition the lens; and
 (d) water.

28. A multi-purpose solution according to claim 27, wherein the galactomannan is selected from the group consisting of guar gum, locust bean gum, tara gum, and chemically modified derivatives thereof.

29. A solution according to claim 28, wherein the concentration of the galactomannan in the solution is 0.1 to 2.0% (w/v).

30. A solution according to claim 27, wherein the galactomannan comprises hydroxypropyl guar.

31. A solution according to claim 30, wherein the concentration of hydroxypropyl guar in the solution is 0.1 to 2.0% (w/v).

32. A solution according to claim 30, wherein the antimicrobial agent is selected from the group consisting of polyquaternium-1 and polyhexamethylene biguanide.

33. A solution according to claim 32, wherein the antimicrobial agent comprises polyquaternium-1.

34. A solution according to claim 27, wherein the antimicrobial agent is selected from the group consisting of polyquaternium-1 and. polyhexamethylene biguanide.

* * * * *